US010386286B2

(12) United States Patent
Daigle et al.

(10) Patent No.: US 10,386,286 B2
(45) Date of Patent: Aug. 20, 2019

(54) METHODS AND SYSTEMS FOR DETERMINING MINIMUM POROSITY FOR PRESENCE OF CLATHRATES IN SEDIMENT

(71) Applicants: Hugh Callahan Daigle, Houston, TX (US); John Thomas Balczewski, Houston, TX (US)

(72) Inventors: Hugh Callahan Daigle, Houston, TX (US); John Thomas Balczewski, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 1350 days.

(21) Appl. No.: 14/081,809

(22) Filed: Nov. 15, 2013

(65) Prior Publication Data

US 2014/0142853 A1    May 22, 2014

Related U.S. Application Data

(60) Provisional application No. 61/727,555, filed on Nov. 16, 2012, provisional application No. 61/727,560, filed on Nov. 16, 2012.

(51) Int. Cl.
*G01N 15/08* (2006.01)
*G01V 9/00* (2006.01)
*E21B 43/01* (2006.01)

(52) U.S. Cl.
CPC .......... *G01N 15/088* (2013.01); *G01V 9/00* (2013.01); *E21B 2043/0115* (2013.01)

(58) Field of Classification Search
CPC .................................................. G01N 15/088
(Continued)

(56) References Cited

U.S. PATENT DOCUMENTS 8,232,428 B2   7/2012   Mousa et al.
9,189,572 B2   11/2015  Miyamoto et al.
(Continued)

FOREIGN PATENT DOCUMENTS

CN    101644781     2/2010
WO    1985/00892    2/1985
WO    2011/122259   10/2011

OTHER PUBLICATIONS

Anderson et al., "Characteristics of Clathrate Hydrate Equilibria in Mesopores and Interpretation of Experimental Data", Feb. 2003, American Chemical Society, J. Phys. Chem. B 2003, 107, pp. 3500-3506.*

(Continued)

*Primary Examiner* — Ricky Ngon
(74) *Attorney, Agent, or Firm* — Andrew J. Lagatta; Melissa M. Hayworth; Marie L. Clapp

(57) ABSTRACT

Methods and systems for determining whether conditions exist for presence of clathrates are disclosed. One method includes determining a thickness of a clathrate stability zone based, at least in part, on a depth at which a temperature reaches a three-phase equilibrium temperature of the clathrates. The method also includes calculating a temperature and a three-phase equilibrium temperature for a range of depths in the clathrate stability zone, and determining a minimum pore size at each of the depths in the range of depths, the minimum pore size permitting a predetermined saturation level of clathrates and based at least in part on the temperature and three-phase equilibrium temperature. The method further includes converting the minimum pore size at each of the depths to a minimum porosity.

10 Claims, 7 Drawing Sheets

(58) Field of Classification Search
USPC .......................................................... 702/2
See application file for complete search history.

(56) References Cited

U.S. PATENT DOCUMENTS

2013/0275090 A1  10/2013  Han
2014/0142853 A1   5/2014  Daigle et al.
2014/0142890 A1   5/2014  Daigle et al.

OTHER PUBLICATIONS

Klauda et al., "Predictions of gas hydrate phase equilibria and amounts in natural sediment porous media", Elsevier, Marine and Petroleum Geology 20 (2003), pp. 459-470.*

Seshadri et al., "Measurements of Equilibrium Pressures and Temperatures for Propane Hydrate in Silica Gels with Different Pore-Size Distributions", Jan. 2001, American Chemical Society, J. Phys. Chem. B 2001, 105, pp. 2627-2631.*

PCT International Search Report and Written Opinion, International App. No. PCT/US2013/070243, dated Aug. 8, 2014.

Anderson, R. et al., Gas hydrate growth and dissociation in narrow pore networks: capillary inhibition and hysteresis phenomena, London, Special Publications, 319, 145-159, The Geological Society of London 2009.

Bennett, Richard H. et al., Geotechnical Properties of Surficial Sediments in a Mega-Corridor: U.S. Atlantic Continental Slope, Rise, and Deep-Sea Basin, Marine Geology, 38 (1980) 123-140, Elsevier Scientific Publishing Co., Amsterdam, NL.

Bhatnagar, G. et al., Generalization of Gas Hydrate Distribution and Saturation in Marine Sediments by Scaling of Thermodynamic and Transport Processes, American Journal of Science, Jun. 2007.

Daigle, Hugh et al., Capillary controls on methane hydrate distribution and fracturing in advective systems, AGU and The Geochemical Society, vol. 12, No. 1, Jan. 19, 2011, Houston, TX.

Dong, Hu et al., Pore-network extraction from micro-computerized-tomography images, Dept. of Earth Science and Engineering, Imperial College, London, UK Sep. 14, 2009.

Duan, Zhenhao et al., The prediction of methane solubility in natural waters to high iconic strength from 0 to 250° C. and from 0 to 1600 bar, Dept. of Chemistry, University of California, San Diego, La Jolla, CA, Jan. 15, 1992.

Ginsburg, G. et al., Sediment Grain-size Control on Gas Hydrate Presence, Sites 994, 995, and 997, Proceedings of the Ocean Drilling Program, Scientific Results, vol. 164, 2000.

Haligva, Cef, Natural Gas Recovery from Hydrates in a Silica Sand Matrix, University of British Columbia, Vancouver, Nov. 2008.

Henry, P. et al., Formation of natural gas hydrates in marine sediments 2. Thermodynamic calculations of stability conditions in porous sediments, Journal of Geophysical Reseach, vol. 104, No. B10, pp. 23,005-23,022 Oct. 10, 1999.

Kraemer, Lisa M. et al., Lithology of the Upper Gas Hydrate Zone, Blake Outer Ridge: A Link Between Diatoms, Porosity, and Gas Hydrates, Dept. of Geological Sciences, University of Michigan, Ann Arbor, MI 2000.

Liu, Xiaoli et al., Capillary effects on hydrate stability in marine sediments, Journal of Geophysical Research, vol. 116, 2011.

Mountain, G.S., Tucholke, B.E, Mesozoic and Cenozoic geology of the US Atlantic continental slope and rise, Geologic Evolution of the United States Atlantic Margin 1985.

Ohmura, Ryo et al., Measurements of clathrate-hydrate film thickness using laser interferometry, Journal of Crystal Growth 218 (2000) 372-380.

Ostergaard, Kasper K. et al., Hydrate phase equilibria in porous media: effect of pore size and salinity, Centre for Gas Hydrate Research, Dept. of Petroleum Engineering, Heriot-Watt University, Edinburgh, UK 2002.

Paull, Charles K. et al., LEG 164 Overview, Geology Department, University of North Carolina at Chapel Hill, Chapel Hill, NC 2000.

Turner, Douglas J. et al., Sensitivity of methane hydrate phase equilibria to sediment pore size, Science Direct, Fluid Phase Equilibria 228-229 (2005) 505-510.

Uchida, Tsutomu et al., Decomposition of methane hydrates in sand, sandstone, clays, and glass beads, Journal of Geophysical Research, vol. 109, 2004.

Waite, W.F. et al.; Physical Properties of Hydrate-Bearing Sediments, American Geophysical Union, Reviews of Geophysics, paper No. 2008RG000279, 2009.

Zeng, Huang et al., Sediment Control on the Saturation Level of Gas Hydrate in Nature Environments, Proceedings of the $6^{th}$ International Conference of Gas Hydrates (ICGH 2008) Vancouver, BC, Canada.

Blunt et al., "Network extraction from sandstone and carbonate pore space images", Sep. 2006, Elsevier, Journal of Petroleum Science and Engineering, pp. 219-231.

Silin et al., "Pore space morphology analysis using maximal inscribed spheres", May 2006, Elsevier, Physcia A 371, pp. 336-360.

Bryant, Steven et al.; "Prediction of Relative Permeability in Simple Porous Media"; The American Physical Society, Aug. 1992, vol. 46, No. 4, pp. 2004-2011.

Hovem, Jens M., et al.; "Viscous Attenuation of Sound in Saturated Sand"; Journal of Acoustical Society of America, Dec. 1979, vol. 66, No. 6, pp. 1807-1822.

Schwartz, Lawrence M., et al.; "Transport Properties of Disordered Continuum Systems"; The American Physical Society; Jun. 1989, vol. 39, No. 16, pp. 11965-11970, and Fig. 1.

International Search Report, dated Aug. 20, 2014; International Application No. PCT/US2013/070246.

Written Opinion of the International Searching Authority, dated Aug. 20, 2014, during the prosecution of International Application No. PCT/US2013/070246.

Behseresht, Javad, et al.; "Infinite-Acting Physically Representative Networks for Capillarity-Cotrolled Displacements"; SPE Journal, Dec. 2009, pp. 568-578.

Bhatnagar, Shalabh; "Adaptive Newton-Based Multivariate Smoothed Functional Alborithms for Simulation Optimization"; ACM Transactions on Modeling and Computer Simulation, Dec. 2007, vol. 18, No. 1, Article 2, pp. 2:1-2.35.

Chen, Liang et al.; "Analysis and Solution for Generation of Hydrates in Oil (Gas) Testing Process of Jinlong Well Four"; English Abstract, one page.

Clennel, M. Ben, et al; "Formation of Natural Gas Hydrates in Marine Sediments 1. Conceptual Model of Gas Hydrate Growth Conditioned by Host Sediment Properties"; Journal of Geophysical Research, Oct. 1999, vol. 104, No. B10, pp. 22,985-23,003.

Ma, Qinglan, et al.; "Modeling of Gas Hydrate Equilibrium Conditions in Porous Media"; Proceedings of the Twenty-Second International Offshore and Polar Engineering Conference, Jun. 2012, pp. 45-52.

Rajaram, Harihar, et al.; "Prediction of Relative Permeabilities for Unconsolidated Soils Using Pore-Scale Network Models"; Water Resources Research, Jan. 1997, vol. 33, No. 1, pp. 43-52.

Patent Examination Report No. 1, dated Nov. 10, 2016, during the prosecution of Australian Application No. 2013344618.

Notification of the First Office Action, dated Oct. 10, 2016, during the prosecution of Chinese Application No. 201380056025.7.

* cited by examiner

METHODS AND SYSTEMS FOR DETERMINING MINIMUM POROSITY FOR PRESENCE OF CLATHRATES IN SEDIMENT

CROSS-REFERENCE TO RELATED APPLICATIONS

The present application claims priority from U.S. Provisional Patent Application No. 61/727,555, filed on Nov. 16, 2012, and U.S. Provisional Patent Application No. 61/727,560, filed on Nov. 16, 2012, the disclosures of each of which are hereby incorporated by reference in their entireties.

TECHNICAL FIELD

The present application relates generally to determining a minimum porosity for the presence of clathrates in a medium. In particular, the present application relates to determining a minimum porosity for the presence of clathrates in sediment, for example using empirical relationships between porosity and observable characteristics.

BACKGROUND

"Clathrates" generally refer to non-stoichiometric metastable substances in which lattice structures composed of first molecular components (host molecules) trap or encage one or more other molecular components (guest molecules) in what resembles a crystal-like structure. Clathrates are sometimes referred to as inclusion compounds, hydrates, gas hydrates, methane hydrates, natural gas hydrates, $CO_2$ hydrates and the like.

In the field of hydrocarbon exploration and development, clathrates are of particular interest. For example, clathrates exist in which water host molecule lattices encage one or more types of hydrocarbon guest molecule(s). Such hydrocarbon clathrates occur naturally in environments of relatively low temperature and high pressure where water and hydrocarbon molecules are present, such as in deepwater and permafrost sediments. Clathrates at lower temperatures remain stable at lower pressures, and conversely clathrates at higher temperatures require higher pressures to remain stable.

It has been shown theoretically and experimentally that clathrates form preferentially in sediments with larger pores. This phenomenon has been ascribed to the Gibbs-Thomson effect, which suppresses nucleation of solids in restricted spaces like the pore space of fine-grained sediments. The Gibbs-Thomson effect may be used to explain observations of clathrate distribution in marine sediments of different grain sizes. However, existing work investigating the Gibbs-Thomson effect has focused solely on explaining reasons for a known presence of clathrates in terms of pore size. A more useful description for geophysical prospecting would be in terms of porosity. However, the relationship between porosity and pore size is complicated and depends on grain shape and packing.

As such, improvements in methods and systems for detecting whether conditions exist for formation of clathrates would be desirable, in particular in the area of hydrocarbon exploration.

SUMMARY

In accordance with the following disclosure, the above and other issues are addressed by the following:

In a first aspect, a method of determining whether conditions exist for presence of clathrates is disclosed. The method includes determining a thickness of a clathrate stability zone based, at least in part, on a depth at which a temperature reaches a three-phase equilibrium temperature of the clathrates. The method also includes calculating a temperature and a three-phase equilibrium temperature for a range of depths in the clathrate stability zone, and determining a minimum pore size at each of the depths in the range of depths, the minimum pore size permitting a predetermined saturation level of clathrates and based at least in part on the temperature and three-phase equilibrium temperature. The method further includes converting the minimum pore size at each of the depths to a minimum porosity.

In a second aspect, a computerized system for determining whether conditions exist for presence of clathrates is disclosed. The system includes a porosity determination component configured to establish a porosity at a plurality of depths in a range of depths in a clathrate stability zone for which the possible presence of clathrates is to be determined. The system also includes a computing system configured to determining whether conditions exist for presence of clathrates. The computing system is configured to execute program instructions which, when executed, cause the computing system to determine a thickness of a clathrate stability zone based, at least in part, on a depth at which a temperature reaches a three-phase equilibrium temperature of the clathrates, and calculate a temperature and a three-phase equilibrium temperature for the plurality of depths in the clathrate stability zone. The computing system is further configured to determine a minimum pore size at each of the plurality of depths in the range of depths, the minimum pore size permitting a predetermined saturation level for clathrates and based at least in part on the temperature and three-phase equilibrium temperature, and convert the minimum pore size at each of the plurality of depths to a minimum porosity.

In a third aspect, a computer-readable storage media is disclosed that includes computer-executable instructions which, when executed, cause a computing system to perform a method of determining whether conditions exist for presence of clathrates. The method includes determining a thickness of a clathrate stability zone based, at least in part, on a depth at which a temperature reaches a three-phase equilibrium temperature of the clathrates, and calculating a temperature and a three-phase equilibrium temperature for a range of depths in the clathrate stability zone. The method also includes determining a minimum pore size at each of the depths in the range of depths, the minimum pore size permitting a predetermined saturation level for clathrates and based at least in part on the temperature and three-phase equilibrium temperature. The method further includes converting the minimum pore size at each of the depths to a minimum porosity.

DETAILED DESCRIPTION

As briefly described above, embodiments of the present invention are directed to methods and systems for determining a minimum porosity at which the presence of clathrates of a predetermined saturation may exist at a particular location. In particular, embodiments discussed herein use empirical relationships to existing, observable phenomena to provide a basis for calculating porosity, and in turn, a probability of the existence of clathrates of a sufficient saturation.

For the purposes of this disclosure, the term "clathrate" will include any and all types of lattice (host) molecule(s) and any and all types of encaged (guest) molecule(s) in all possible combinations. Clathrates can include, for example, transitions between various clathrate lattice structure types; formation, stable state and dissociation, and the substitution of one or more type(s) of molecule by one or more other type(s) of molecule.

The methods and systems described herein allow for rapid determination of whether clathrates should be expected to be present in specific sediment areas, such as marine sediments, and therefore provides a prospecting tool both for resource evaluation and geophysical modeling of clathrate deposits. The methods and systems described herein reduce subsurface uncertainty and improve geophysical modeling techniques, providing resource assessment with increased accuracy.

Figure 1:
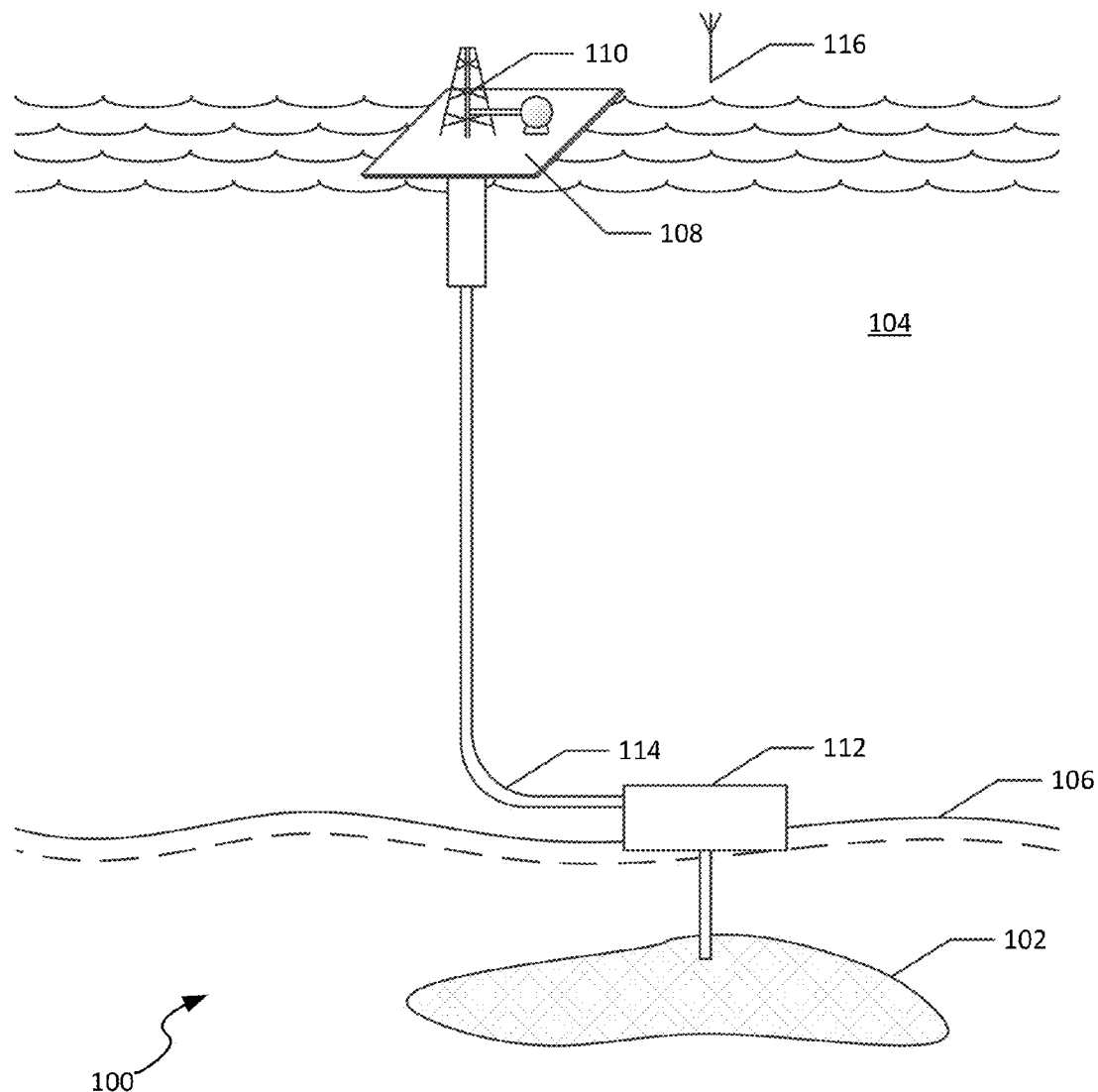
FIG. 1 is a schematic illustration of an offshore hydrocarbon production system including a production facility which receives and processes hydrocarbons from one or more clathrate reservoirs.

FIG. 1 is a schematic drawing of an example embodiment of an offshore or deepwater hydrocarbon production system 100. System 100 includes a clathrate reservoir 102 disposed beneath sea water 104 and seafloor 106. This clathrate reservoir 102 produces water and hydrocarbons, primarily natural gas. In the embodiment shown, an offshore platform 108 supports a production facility 110, which is used to at least partially separate liquids, water and/or oil, from natural gas.

In this example embodiment, the clathrate reservoir 102 is shown in fluid communication with a subsea well 112 which, in turn, is connected to production facility 110 by way of tieback 114. Clathrate reservoir 102 primarily produces a mixture of natural gas and water which is delivered to production facility 110 for separation of natural gas and water, and oil if there are significant amounts of oil contained within the mixture.

It is noted that, in the embodiment shown in FIG. 1, a wave generation and detection system 116 can be used prior to installation of the overall hydrocarbon production system 100, and can be used to locate the system 100 at a particular location along the seafloor 106. The wave generation and detection system 116 can be, for example a seismic or other acoustic wave generation system, or other system capable of generating waves that are able to penetrate the sea water 104 and seafloor 106, and to capture reflected waves, and thereby detect differences in the media through which the waves travel based on speed of travel.

It is noted that the production system 100 shown in FIG. 1 is only an exemplary embodiment. Those skilled in the art will appreciate that it is within the scope of the present invention to provide a hydrocarbon production system that combines multiple such clathrate reservoirs and associated wells, or combination of such a clathrate reservoir and associated well with conventional hydrocarbon reservoir and well systems. An example of such a system is illustrated in U.S. Pat. No. 8,232,428, filed Aug. 25, 2008, the disclosure of which is hereby incorporated by reference in its entirety.

Figure 2:
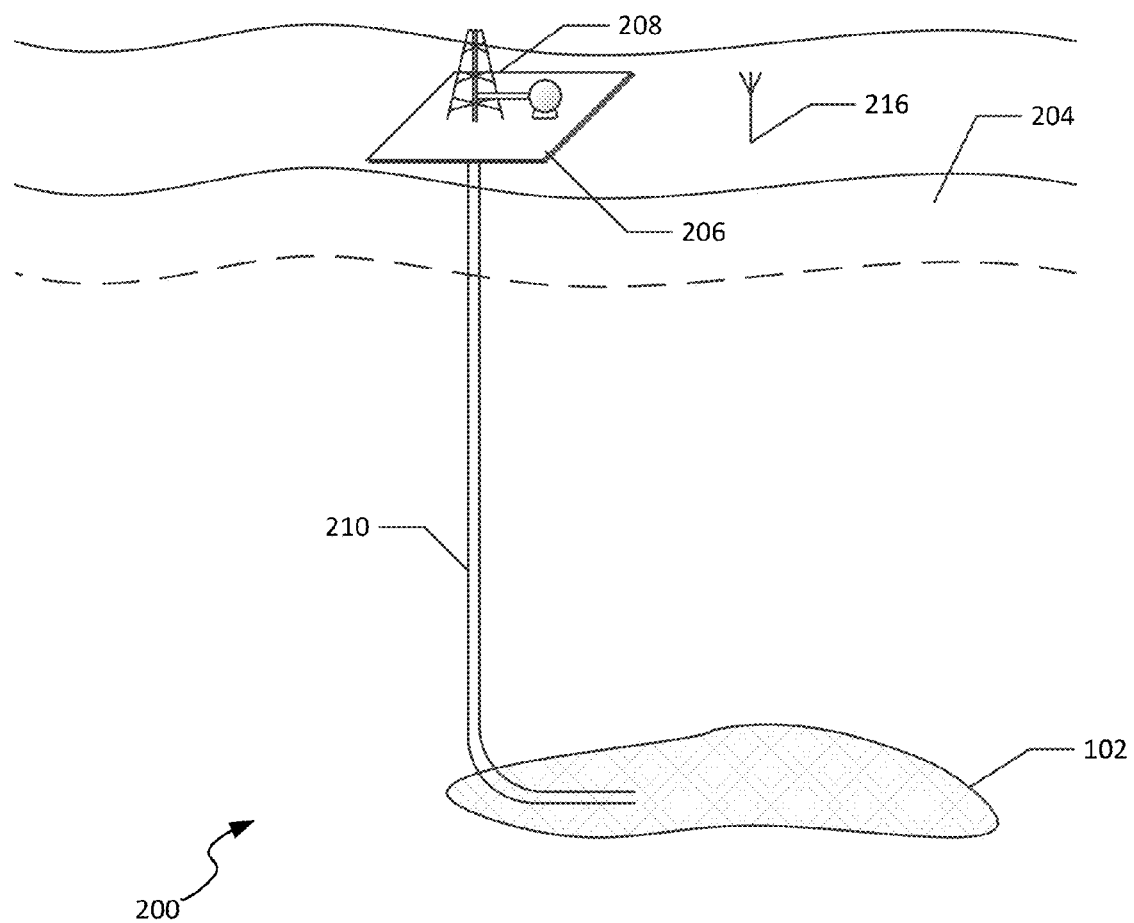
FIG. 2 is a schematic illustration of an onshore hydrocarbon production system including a production facility which receives and processes hydrocarbons from one or more clathrate reservoirs.

FIG. 2 is a schematic drawing of another exemplary embodiment of a hydrocarbon production system 200 which, in this case, is located on land rather than being based offshore. Production system 200 includes a clathrate reservoir 202. Disposed upon a permafrost layer 204 is an arctic platform 206. A production facility 208, generally similar to production system 110, is located atop arctic platform 206. Production facility 208 is used to separate and process natural gas, oil and water received from the clathrate reservoir 202. Production tubing 210 is used to fluidly convey a mixture of clathrates and water from clathrate reservoir 202 to arctic platform 206 and production facility 208. The mixture may include, in some cases, a small portion of oil.

As with the hydrocarbon production system 100 of FIG. 1, it is noted that in the context of the on-land arrangement of FIG. 2, a wave generation and detection system 216, analogous to system 116 of FIG. 1, can be used prior to installation of the overall hydrocarbon production system 200, and can be used to locate the system 200 at a particular location. The wave generation and detection system 216 can include any of a variety of types of seismic, acoustic, or other system capable of generating waves that are able to penetrate the permafrost layer 204, and to capture reflected waves, and thereby detect differences in the media through which the waves travel based on speed of travel. It is noted that, in the example of FIG. 2, there are likely to be greater variations in densities at shallower depths, based on the comparative uniformity of sea water as compared to variations found in the on-land subsurface sediments. In either case, such data can be captured for use in some embodiments of the present disclosure, as discussed in further depth below.

Figure 3:
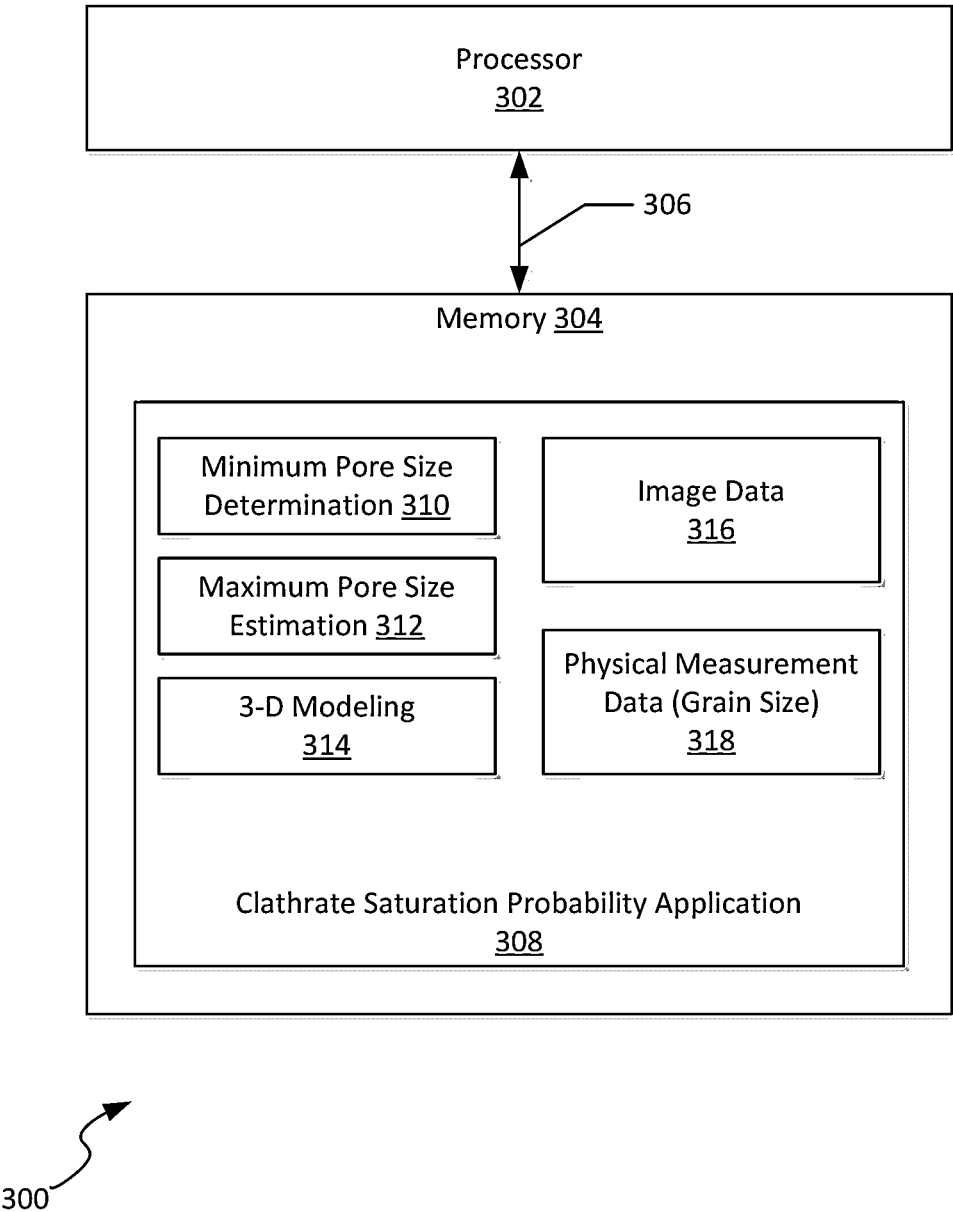
FIG. 3 is a schematic illustration of a computing system in which a probability of the presence of clathrates of a predetermined concentration can be calculated.

Referring now to FIG. 3, an example computing system 300 is illustrated that can be used to calculate whether conditions exist for presence of clathrates, such as can be used to locate a production system such as those shown in FIGS. 1-2. In general, the computing system 300 includes a processor 302 communicatively connected to a memory 304 via a data bus 306. The processor 302 can be any of a variety of types of programmable circuits capable of executing computer-readable instructions to perform various tasks, such as mathematical and communication tasks.

The memory 304 can include any of a variety of memory devices, such as using various types of computer-readable or computer storage media. A computer storage medium or computer-readable medium may be any medium that can contain or store the program for use by or in connection with the instruction execution system, apparatus, or device. In the context of the present disclosure, a computer storage medium includes at least some tangible component, i.e., is not entirely consisting of transient or transitory signals. In the embodiment shown, the memory 304 stores a clathrate saturation probability analysis application 308. The clathrate saturation probability analysis application 308, when executed, can be used to calculate or determine whether conditions exist for the presence of clathrates of a predetermined concentration. For example, the application 308 can calculate a thickness of a clathrate stability zone, i.e., a range of depths at which pressures and temperatures are such that clathrate formation is possible. The application 308 can also compute an in situ temperature and a three-phase equilibrium temperature for clathrate phases within the calculated clathrate stability zone.

In some embodiments, the application 308 includes a number of components computer-executable code including a minimum pore size determination component 310, a maximum pore size estimation component 312, and optionally a three-dimensional modeling component 314. The minimum pore size determination component 310 is configured to determine a minimum pore size supporting a predetermined clathrate saturation based at least in part on the in situ temperature and the three-phase equilibrium temperature. The predetermined clathrate saturation can be, for example, a desirable clathrate saturation selectable by a user. In some embodiments, the minimum pore size determination component 310 also calculates the thickness of the clathrate stability zone and three-phase and in situ temperatures, in place of the application 308 overall. In such cases, the thickness of the stability zone may be based on the particular type of clathrate (e.g., methane hydrates, etc.) to be detected, and can be based at least in part on observed temperatures and pressures across a range of subsurface depths (e.g., from a different test well or other historical knowledge of an area). The minimum pore size determination component 310 is also configured to calculate a minimum pore radius in which clathrates of the given concentration can be formed. This calculation can be, for example based on the Gibbs-Thompson effect.

The Gibbs-Thomson effect is a depression in the freezing point of a solid nucleating out of liquid solution within a restricted spatial domain. In other words, the effect describes the difficulty in forming a solid in appropriate temperature/pressure conditions due to a confined space in which the conditions are experienced. As applied herein, the change in freezing point noted by the Gibbs-Thompson effect, cited herein as $\Delta T_f[K]$, is given by:

$$\Delta T_f = -T_{f,h}(F\gamma_{s1}/r\rho_s\Delta H_{s1})$$

In this equation, $T_{f,h}$ is the freezing point in bulk solution [K], F is a geometric factor, $\gamma_{s1}$ is the interfacial energy of the solid-liquid interface [J/m$^2$], r is the spatial dimension of the restricted space [m], $\rho_s$ is the bulk density of the solid phase [kg/m$^3$], and $\Delta H_{s1}$ is the latent heat of fusion of the solid phase [J/mol]. For clathrate-bearing sediments, $T_{f,h}$ represents the three-phase equilibrium temperature for solid clathrate-dissolved gas-free gas, and r is the pore radius. In the case where the clathrates under consideration are methane hydrates, relevant parameters included in the above-described equation include: $\gamma_{s1}$=0.27 J/m3, $\rho_s$=930 kg/m3, and $\Delta H_{s1}$=54.5 kJ/mol. Additionally, parameter F is equal to 2, which is a value that generally is representative of both cylindrical and spherical pores. The Gibbs-Thompson effect, as applied to porous sediments in the present disclosure, is discussed below in connection with FIG. 4.

The maximum pore size estimation component 312 is configured to empirically determine a maximum pore size that is to be expected in a clathrate stability zone. In other words, the component 312 is configured to, for example, estimate a maximum pore size based on observations or detection processes available other than direct measurement, such as through use of the acoustic or seismic wave transmission and capture of reflected waves, as discussed above in connection with FIGS. 1-2.

In some embodiments, the application 308 can further include a three-dimensional data modeling component 314. The three-dimensional data modeling component 314 can be configured to model, in a particular volume, a distribution of grains of varying sizes, and can be used by the maximum pore size estimation component 312 to determine a maximum pore size based on the model built in the three-dimensional data model. Further details regarding such modeling are discussed in further detail in U.S. Provisional Patent Application No. 61/727,567, filed Nov. 16, 2012 and entitled "Methods and Systems for Determining Pore Size in Sediment Using Physical Measurement of Sediment Samples", U.S. Provisional Patent Application No. 61/727,569, filed Nov. 16, 2012 and entitled "Methods and Systems for Determining Pore Size in Sediment Using Numerical Modeling", and U.S. patent application Ser. No. 14/081,838, filed the same day herewith and entitled "Methods and Systems for Determining Pore Size in Sediment", the disclosures of each of which are incorporated by reference in their entireties.

Optionally, in some embodiments the memory 304 can also include an empirical data analysis module 316 and a physical measurement data module 318. The empirical data analysis module 316 contains one or more models of sediment properties, and can include or receive data regarding a particular type or sample of sediment. For example, the empirical data analysis module 316 can be used alongside the maximum pore size estimation component 312 to determine a maximum pore size based on, for example, historical data, or sample data, or other types of empirical data.

The physical measurement data module 318 is capable of receiving physical measurements of subsurface sediments and performing any of a variety of physical measurement processes, as are described herein. This can include any of a variety of direct physical measurements, such as laser particle size analysis, Stokes settling analysis, image analysis, or other techniques, to determine a distribution of particle sizes in a particular sample.

In addition, the application 308 can include a comparison component or otherwise be configured to compare the determined maximum pore size with the minimum pore size supporting the predetermined clathrate saturation to determine whether the predetermined clathrate saturation is possible in the clathrate stability zone. Based on such a comparison of the output of components 310, 312, it can be determined whether such a concentration of clathrates is possible, and therefore whether direct underground exploration is worth pursuing.

Referring to FIG. 3 overall, it is noted that other modules or features could be incorporated into such a computing system 300 overall, or into an application such as application 308. Furthermore, although it is noted that some components or modules include specified functionality, this functionality could generally also be said to reside within the application 308 overall, or could be implemented across a multi-processor system, or multi-computer network.

Figure 4:
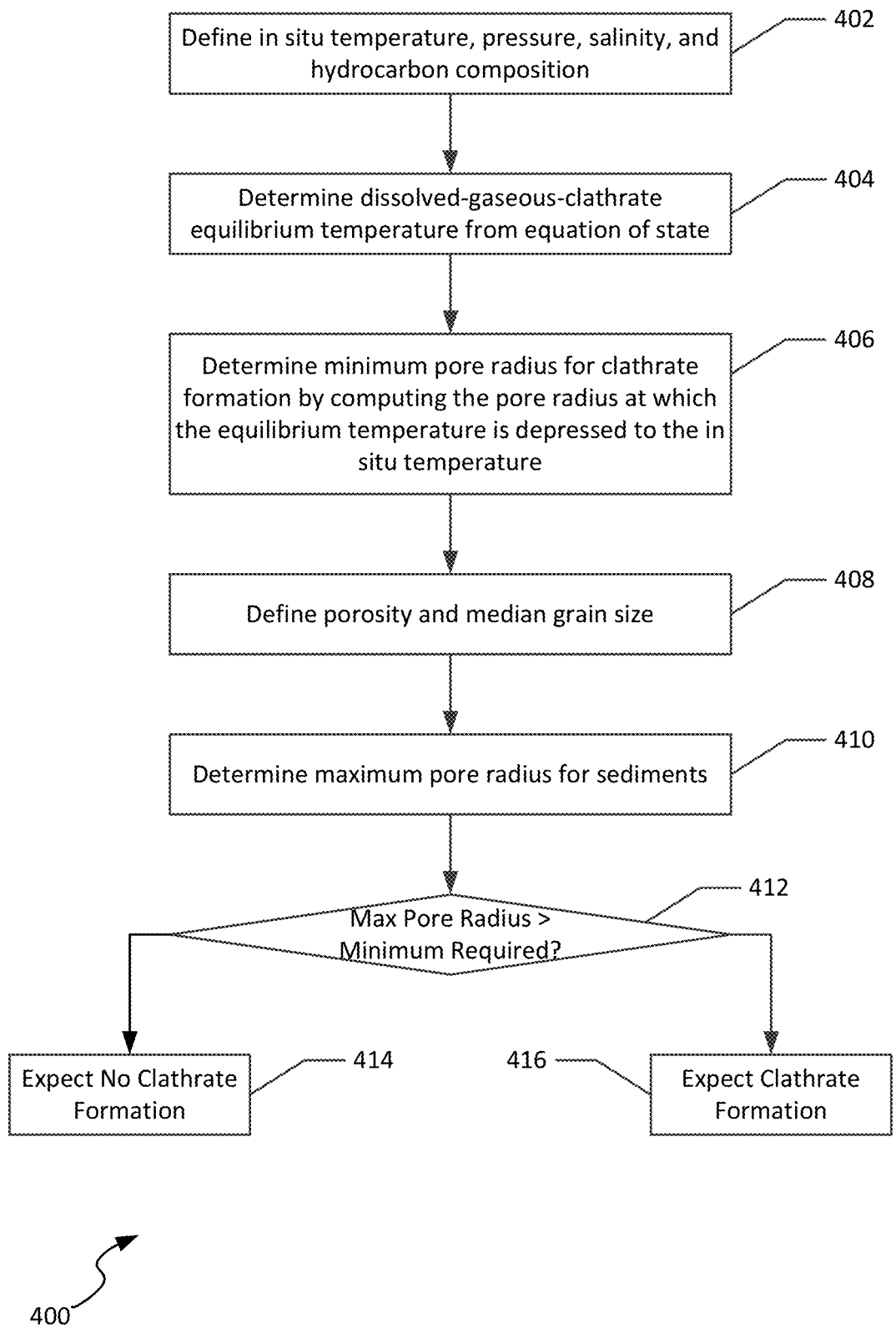
FIG. 4 is a flowchart illustrating an example method of determining whether conditions exist for presence of clathrates, according to an example embodiment of the present disclosure.

Referring now to FIG. 4, a flowchart is depicted that illustrates an example method 400 for determining a minimum porosity required for the presence of clathrates. In particular, the method 400 is generally useable in connection with a packing of randomly-sized sediment particles, modeled as spheres, using empirical relationships between grain size and pore size.

In the embodiment shown, the method 400 is initiated by computing a thickness of a clathrate stability zone, given a known seafloor temperature and depth, as well as a known geothermal gradient, salinity, and clathrate composition (step 402). In particular, each of these features is discernible by direct measurement, and for which an exact thickness can be computed. Although in general such zones can vary in depth, typical clathrate stability zones are formed at depths of about 800 meters or less.

The method 400 also includes computing an in situ temperature and three-phase equilibrium temperature for the dissolved, gaseous, and clathrate phases over the stability zone, to determine a point at which such clathrates would or would not exist (step 404). In various embodiments, the calculated temperatures are determined at a variety of depths in the clathrate stability zone, for example based on observed temperatures and pressures across the range of subsurface depths at other locations. In some embodiments, the method 400 can also include direct measurement of temperatures at a seafloor, or otherwise in proximity to the calculated clathrate stability zone.

In some embodiments, three three-phase equilibrium temperature is based at least in part on a depth of the sea floor, a hydrostatic gradient, and seawater salinity. Furthermore, in some embodiments, the in situ temperature is computed from the seafloor temperature and geothermal gradient, and the three-phase equilibrium temperature is computed from the equation of state provided in Duan, Z. H., et al, "The Prediction of Methane Solubility in Natural Waters to High Ionic Strength from 0 to 250 C and from 0 to 1600 Bar", Geochimica et Cosmochimica Acta, 56, 1451-1460, 1992. This calculation uses the seafloor depth and assuming a hydrostatic gradient and seawater salinity. The depth at which the two temperatures are equal is determined iteratively with a Newton-Raphson algorithm to use an iterative process to approach one root of a function. In some embodiments, following the method described in "Adaptive Newton-Based Multivariate Smoothed Functional Algorithms for Simulation Optimization", Bhatnagar, S., Jour. ACM Trans. on Mod. and Comp. Sim., Vol. 18, Issue 1, (2007). Other types of processes to determine the depth at which in situ and three-phase equilibrium temperatures are equal may be used as well.

Once the thickness of the clathrate stability zone and both the in situ and three-phase equilibrium temperatures are known, the minimum pore size determination component 310 computes a minimum porosity that would permit a user-selected clathrate saturation over the range of depths that make up the clathrate stability zone (step 406). In some embodiments, this is calculated from the difference between in situ temperature and three-phase equilibrium temperature using equations describing the Gibbs-Thomson effect.

In particular, the minimum porosity that would support a particular saturation of clathrates at a given depth depends, at least in part, upon the three phase temperature at the depth, as well as a geometric factor, interfacial energy of a solid-liquid interface, bulk density of clathrates in a solid phase, latent heat of fusion of solid phase clathrates, and pore radius. Based on the above equation $\Delta T_f = -T_{f,h}(F\gamma_{sl}/r\rho_s \Delta H_{s1})$, and assuming that the parameter F is equal to 2, which is a value generally representative of both cylindrical and spherical pores, the specific pore radius will generally decrease as concentration of clathrates increases. In particular, assuming clathrates grow in the pores and as a coating around spherical grains, the pore radius will be reduced by a factor of $(1-S_c)^{1/3}$, where $S_c$ is the clathrate saturation, or volume fraction of pore space occupied by clathrate. Using this modification, the difference between in situ temperature and three-phase equilibrium temperature can be expressed in terms of clathrate saturation using the following equation (assuming $r_0$ is the initial (clathrate free) pore radius):

$$\Delta T_f = -T_{f,h}(F\gamma_{s1}/r_0(1-S_c)^{1/3}\rho_s \Delta H_{s1})$$

Notably, as clathrate grows in the sediment pore space, the three phase equilibrium temperature will be depressed until it reaches the local, in situ temperature, at which clathrate should stop forming since it is no longer the only stable phase. Therefore, given an in situ temperature and three phase equilibrium temperature, the minimum initial porosity that will permit a selected clathrate saturation $S_c$ can be computed by the minimum pore size determination component 310, in step 406, from the following equation:

$$r_0 = T_{f,b}F\gamma_{s1}/((T_{f,b}-T)(1-S_c)^{1/3}\rho_s \Delta H_{s1})$$

Once the minimum porosity is determined in step 406, a median porosity and a median grain size can be determined (step 408). This can be accomplished, for example, using a maximum pore size component 312. For a cubic packing of equally spheres with radius r separated by a distance $2a$, the radius of an inscribed sphere $r_s$ in the pore created by 8 neighboring spheres is represented as:

$$r_s = \left(\frac{3}{2}\sqrt{2} - 1\right)r + \frac{3}{2}\sqrt{2}\, a$$

Additionally, a void ratio e of the medium can be represented by:

$$e = \frac{6}{\pi}\left(1 + \frac{a}{r}\right)^3 - 1$$

Based on these equations, a ratio of the inscribe sphere radius $r_s$ to the packing of spheres having a radius r, or $r_s/r$, is expressed as a void ratio as follows:

$$\frac{r_s}{r} = \frac{3}{2}\sqrt{2} - \frac{5}{2} + \frac{3}{2}\left(\frac{\pi}{6}(e+1)\right)^{1/3}$$

In terms of porosity, which is illustrated as $\varphi(e=\varphi)/(1-\varphi))$, the above equation can be re-cast as follows:

$$\frac{r_s}{r} = \frac{3}{2}\sqrt{2} - \frac{5}{2} + \frac{3}{2}\left(\frac{\pi}{6}\left(\frac{\varphi}{1-\varphi}+1\right)\right)^{1/3}$$

On the basis of the above equation, this ratio of $r_s$ to r can be rewritten as a function of the form:

$$\frac{r_s}{r} = A\left(\frac{\varphi}{1-\varphi}\right)^B$$

In terms of a median sediment grain diameter $D_{50}$, this can be recast as:

$$\frac{r_s}{D_{50}} = A\left(\frac{\varphi}{1-\varphi}\right)^B$$

In some embodiments, the application 308 applies the above equation and considers median grain diameters, $D_{50}$, of 1, 10, 50, and 100 microns, which is a range representative of most marine sediments. Using these grain sizes in the above equation, graphs describing porosity at various depths can be generated, showing the relationship between pore size and clathrate saturations that would be supported.

Figure 5:
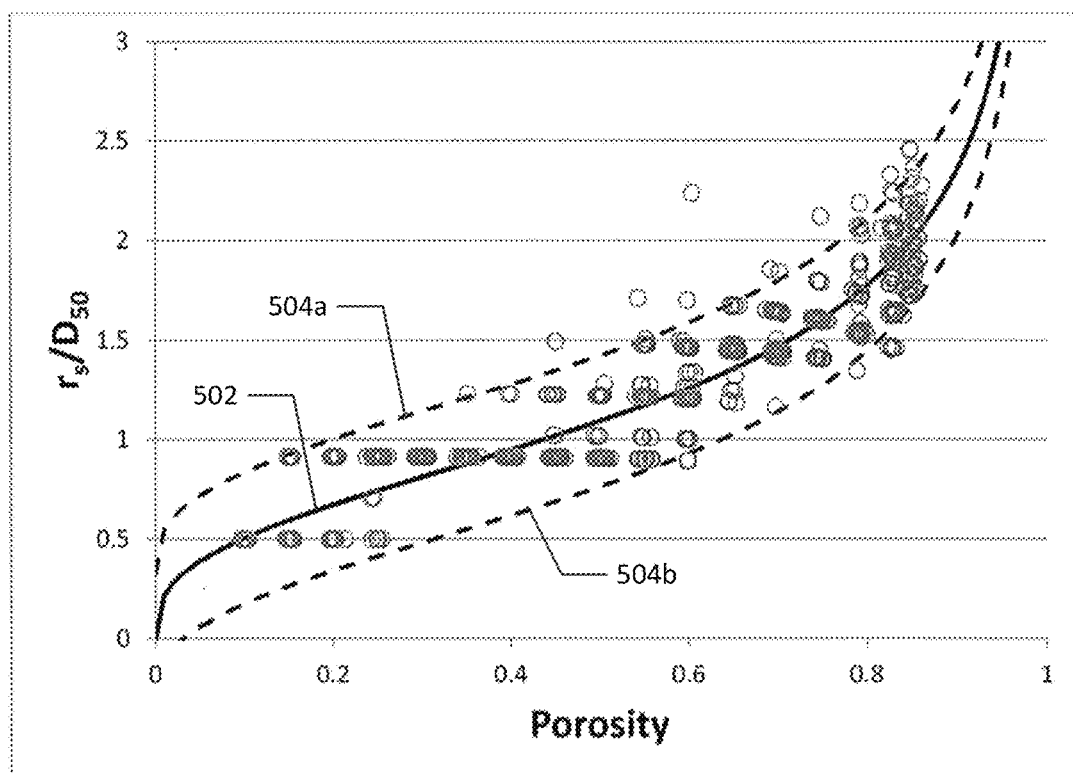
FIG. 5 is a chart illustrating a relationship between relative sizes of sediment grains and inscribed spheres simulating formation of clathrates, and porosity of the medium.
Figure 7:
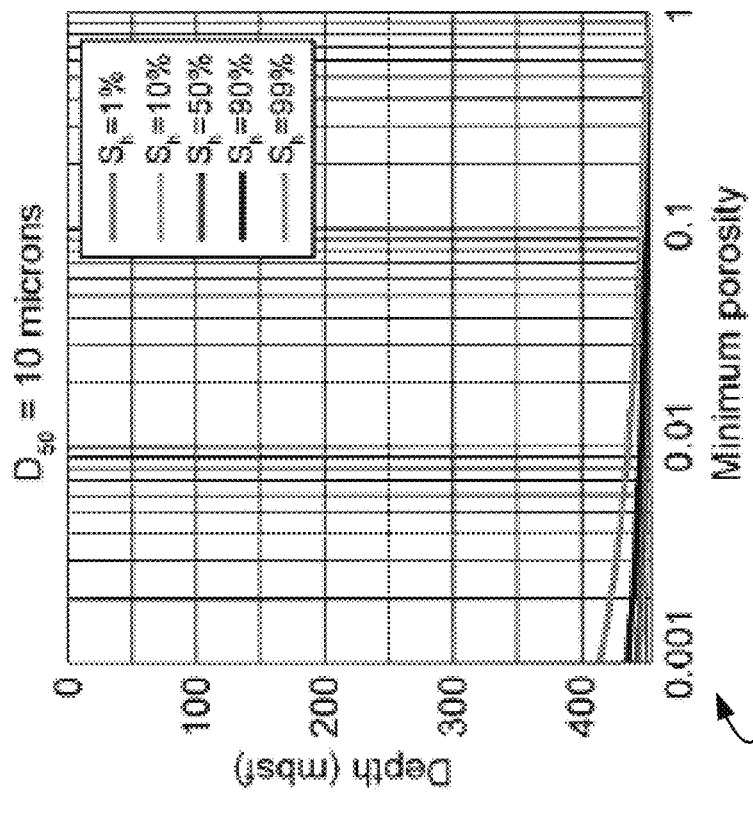
FIG. 7 is a chart illustrating experimental results showing a minimum porosity at which particular concentrations of clathrates may form at different depths, assuming a median grain size of ten microns.
Figure 6:
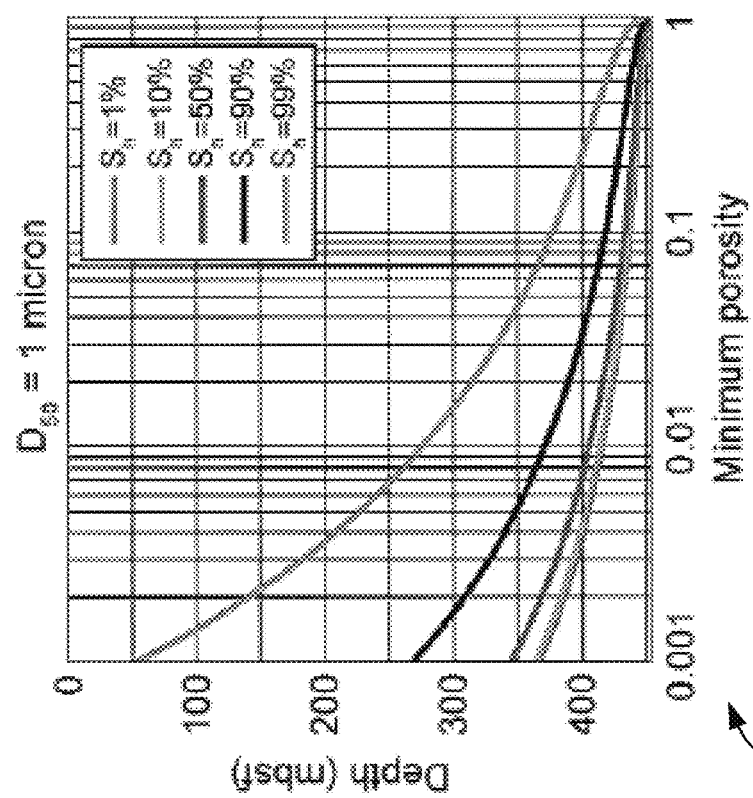
FIG. 6 is a chart illustrating experimental results showing a minimum porosity at which particular concentrations of clathrates may form at different depths, assuming a median grain size of one micron.
Figure 9:
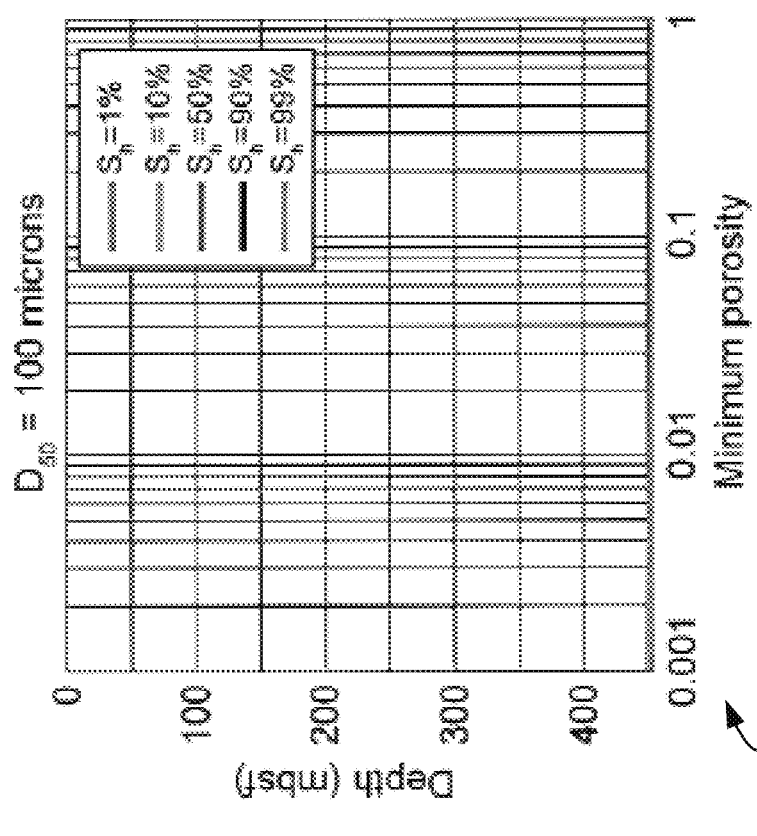
FIG. 9 is a chart illustrating experimental results showing a minimum porosity at which particular concentrations of clathrates may form at different depths, assuming a median grain size of one hundred microns.
Figure 8:
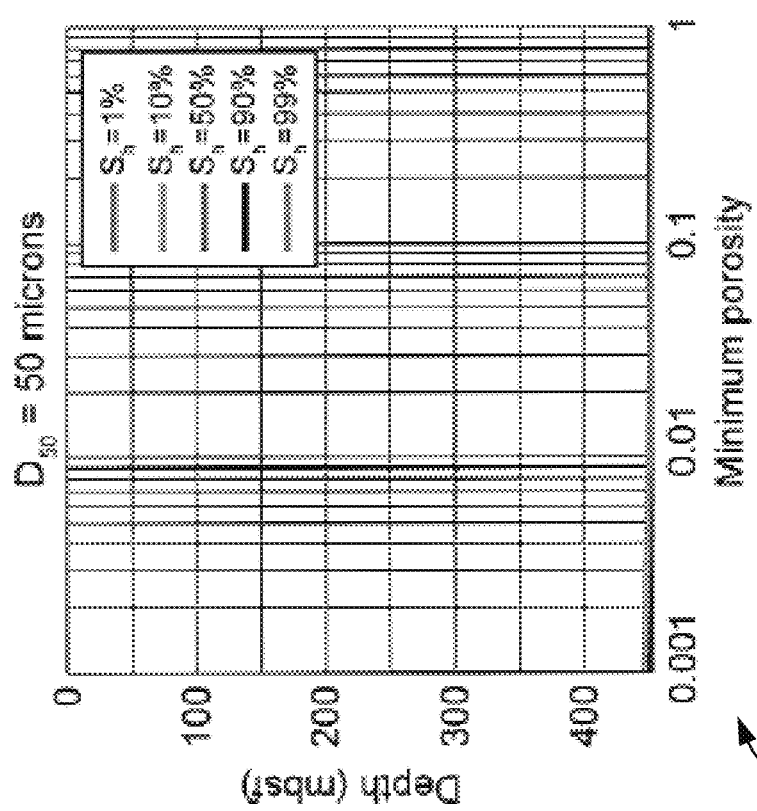
FIG. 8 is a chart illustrating experimental results showing a minimum porosity at which particular concentrations of clathrates may form at different depths, assuming a median grain size of fifty microns.

In a porous medium with a range of grain and pore sizes, the presence or absence of clathrate will be affected by the size of the largest pore. On the basis of 850 simulations of packings of randomly sized spheres, it has been experimentally found that in the above equation, A=1.0913, and B=0.3503. Accordingly, and as seen in FIG. 5, a chart 500 illustrates this example simulation data and regression curve 502 representing a relationship between porosity and the relative radius of an inscribed sphere $r_s$ and median grain size $D_{50}$. Porosity is generally represented on a scale between 0 and 1, with 0 representing no porosity and 1 representing complete porosity. Dotted lines 504a-b represent 95% confidence intervals from the regression curve 502.

Referring now to FIGS. 6-9, results of analysis using parameters for Blake Ridge are depicted. Blake Ridge is a heavily studied methane hydrate deposit located off the shore of South Carolina, in the Atlantic Ocean. In this region, temperature and pressure conditions are at 2781 m of water depth, with seafloor temperature of 276.4 K, and geothermal gradient of 0.04 K/m. As illustrated in FIGS. 6-9, for median grain diameters greater than 10 microns (e.g., as illustrated in graphs 700, 800, 900 of FIGS. 7-9), the pore size has little effect on the presence of hydrate. However, with a median grain diameter of 1 micron as shown in chart 600 of FIG. 6, hydrate will generally not form in the lowest 8 meters of the clathrate stability zone if porosity is less than about 50%. This is significant, because this is the approximate grain size and porosity of the sediments at this depth.

Additionally, and referring back to FIG. 4, the maximum pore size that can be expected in the sediments in question can also be determined from a grain size distribution (step 410). In some embodiments, the maximum pore size can be computed using the maximum pore size component 312 and three-dimensional data modeling component 314. A variety of methods of determining a maximum pore size are possible. In some embodiments, maximum pore size can be determined by modeling an example volume with sediment grains of varying size, and subsequently simulating inscribing a sphere in voids positioned between such grains. Examples of such arrangements are illustrated in U.S. Provisional Patent Application No. 61/727,567, filed Nov. 16, 2012 and entitled "Methods and Systems for Determining Pore Size in Sediment Using Physical Measurement of Sediment Samples", and U.S. Provisional Patent Application No. 61/727,569, filed Nov. 16, 2012 and entitled "Methods and Systems for Determining Pore Size in Sediment Using Numerical Modeling", the disclosures of which were previously incorporated by reference in their entireties.

In some such embodiments, determining maximum pore size could be performed by the maximum pore size component 312, such as through a laser particle size analysis, stokes settling analysis, image analysis, or other techniques to obtain a grain size distribution. Data associated with the median grain size and porosity can then be stored, for example, by the application 308 as physical measurement data by the physical measurement data module 318. In such embodiments, the maximum pore size can be determined using empirical relationships. This can be based, for example, on existing empirical relationships between particle type/size and other observable phenomena. For example, this process can include estimating a pore size based on attenuation of acoustic waves reflected by subsurface sediment. Generally, acoustic waves will travel at faster speeds through materials of higher density, and at lower speeds through materials of lower density. By performing an acoustic analysis of subsurface conditions at a particular location, and comparing the observed reflected wave values to analogous values in areas having a known maximum pore size, such maximum pore sizes that can be expected in a sediment can be determined. For example, maximum pore size expected in the sediments can be based on empirical relationships such as that discussed in "Viscous attenuation of sound in saturated sand", Hovem, J. M., and Ingram, G. D., J. Acoust. Soc. Am., 67, 1559-1563 (1979), the disclosure of which is hereby incorporated by reference in its entirety.

Once the maximum pore size is determined in step 410, and the minimum pore size supporting a particular concentration is calculated in step 406, the two values can be compared (step 412). If the maximum pore size is below the minimum required pore size, the application can thereby determine that the area under consideration cannot support clathrate formation of the desired saturation (step 414). Accordingly, a user could proceed with different analysis, for example by directing the application to analyze a different subsurface area, or adjusting a desired clathrate concentration for use in the analysis (thereby restarting at least a portion of the method illustrated in FIG. 4, using the application 308 of FIG. 3). Conversely, if the maximum pore size of the area under consideration is greater than the minimum pore size required to support clathrate formation at or above a given concentration, then clathrate formation will be possible, and the application 308 will notify a user accordingly (step 416). As such, the user can indicate that the particular location under consideration is a possible candidate location for clathrate harvesting, such as through use of the systems of FIGS. 1-2, described above.

Referring now to FIGS. 3-4, and in particular computing systems embodying the methods and systems of FIG. 4, it is noted that various computing systems can be used to perform the processes disclosed herein. For example, embodiments of the disclosure may be practiced in various types of electrical circuits comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, aspects of the methods described herein can be practiced within a general purpose computer or in any other circuits or systems.

Embodiments of the present disclosure can be implemented as a computer process (method), a computing system, or as an article of manufacture, such as a computer program product or computer readable media. The computer program product may be a computer storage media readable by a computer system and encoding a computer program of instructions for executing a computer process. Accordingly, embodiments of the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media. Further, the disclosed methods' stages may be modified in any manner, including by reordering stages and/or inserting or deleting stages, without departing from the overall concept of the present disclosure.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A method of determining whether conditions exist for presence of clathrates, the method comprising:
   forming particles at each of a plurality of randomly-selected particle locations by modeling growth of particles at each particle location until each particle contacts one or more neighboring particles;
   at each point unoccupied by a particle, inscribing a sphere and determining a size of the sphere, wherein each sphere represents a clathrate;
   determining a maximum size from among the spheres inscribed at each unoccupied point, thereby determining a maximum pore size;
   determining a porosity based on the maximum pore size;
   determining a thickness of a clathrate stability zone based, at least in part, on a depth at which a temperature reaches a three-phase equilibrium temperature of the clathrates;
   calculating a temperature and a three-phase equilibrium temperature for a range of depths in the clathrate stability zone;
   determining a minimum pore size at each of the depths in the range of depths, the minimum pore size permitting a predetermined saturation level of clathrates and based at least in part on the temperature and three-phase equilibrium temperature;
   converting the minimum pore size at each depth to a minimum porosity;
   comparing the minimum porosity to the porosity to determine whether conditions exist for presence of clathrates; and
   installing a hydrocarbon production system at a location based at least in part on a determination that conditions exist for presence of clathrates.

2. The method of claim 1, wherein the temperature is determined based at least in part on a geothermal gradient and an observed temperature at a sea floor.

3. The method of claim 2, wherein the three-phase equilibrium temperature is based at least in part on a depth of the sea floor, a hydrostatic gradient, and seawater salinity.

4. The method of claim 2, further comprising obtaining the observed temperature in proximity to a location for which a possible presence of clathrates is considered.

5. The method of claim 1, wherein determining the thickness of the clathrate stability zone is based at least in part on the clathrates to be detected.

6. The method of claim 1, wherein the particles have a plurality of different median particle sizes.

7. The method of claim 1, wherein the porosity is based on a median particle size.

8. The method of claim 1, wherein determining a maximum pore size includes estimating a pore size based on attenuation of acoustic waves reflected by subsurface sediment.

9. The method of claim 1, further comprising determining a minimum pore size at each of the depths in the range of depths for each of a plurality of different predetermined saturation levels of clathrates.

10. The method of claim 1, wherein determining the minimum pore size at a depth from among the range of depths that permits a predetermined saturation level of clathrates depends, at least in part, upon the three-phase equilibrium temperature at the depth, a geometric factor, interfacial energy of a solid-liquid interface, bulk density of clathrates in a solid phase, latent heat of fusion of solid phase clathrates, and pore radius.

\* \* \* \* \*